United States Patent
Asselin et al.

(10) Patent No.: US 6,245,799 B1
(45) Date of Patent: Jun. 12, 2001

(54) [(INDOL-3-YL)-CYCLOALKYL]-3-SUBSTITUTED AZETIDINES FOR THE TREATMENT OF CENTRAL NERVOUS SYSTEM DISORDERS

(75) Inventors: Magda Asselin, Mahwah; John W. Ellingboe, Ridgewood, both of NJ (US); Richard E. Mewshaw, King of Prussia, PA (US)

(73) Assignee: American Home Products Corp, Madison, NJ (US)

( * ) Notice: Subject to any disclaimer, the term of this patent is extended or adjusted under 35 U.S.C. 154(b) by 0 days.

(21) Appl. No.: 09/707,146

(22) Filed: Nov. 6, 2000

Related U.S. Application Data

(60) Provisional application No. 60/228,811, filed on Nov. 8, 1999.

(51) Int. Cl.[7] .................. A61K 31/404; C07D 209/10
(52) U.S. Cl. ........................... 514/414; 548/467
(58) Field of Search .............................. 514/414; 548/467

(56) References Cited

U.S. PATENT DOCUMENTS 4,581,355 * 4/1986 Tahara et al. ...................... 514/212

FOREIGN PATENT DOCUMENTS

WO 9520588    8/1995  (WO) .

* cited by examiner

Primary Examiner—Deborah C. Lambkin
Assistant Examiner—Golam Shameem
(74) Attorney, Agent, or Firm—Joseph M. Mazzarese

(57) ABSTRACT

This invention provides novel compounds and pharmaceutical compositions and methods of using the compounds in the treatment of central nervous system disorders, such as anxiety and depression, the compounds having the formula I:

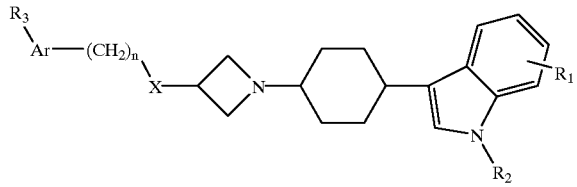

wherein:

X is N—R, O, $S(O)_m$; m is 0 to 2; n is 0 to 4; Ar is an aryl group of 6 to 12 carbon atoms optionally substituted with 1 to 3 $R_3$ groups, or a heteroaryl group of 4 to 10 carbon atoms optionally substituted with 1 to 3 $R_3$ groups;

R and $R_2$ are independently H, straight chain alkyl of 1 to 6 carbon atoms, branched alkyl of 3 to 6 carbon atoms, cycloalkyl of 3 to 6 carbon atoms, alkoxycarbonyl of 1 to 6 carbon atoms, alkylcarbonyl of 1 to 6 carbon atoms, aminocarbonyl, or alkylaminocarbonyl of 1 to 4 carbon atoms;

$R_1$ and $R_3$ are independently H, straight chain alkyl of 1 to 4 carbon atoms, branched alkyl of 3 to 6 carbon atoms, cycloalkyl of 3 to 8 carbon atoms, halo, alkoxy group of 1 to 4 carbon atoms, haloalkyl of 1 to 4 carbon atoms, OH, nitro, amino, sulfonyl, CN, carboxy, alkoxycarbonyl of 1 to 4 carbon atoms, alkylcarbonyl of 1 to 4 carbon atoms, aminocarbonyl, or alkylaminocarbonyl of 1 to 4 carbon atoms;

or a pharmaceutically acceptable salt thereof.

28 Claims, No Drawings

[(INDOL-3-YL)-CYCLOALKYL]-3-SUBSTITUTED AZETIDINES FOR THE TREATMENT OF CENTRAL NERVOUS SYSTEM DISORDERS

This application claims the benefit of U.S. Provisional Application No. 60/228,811, which was converted from U.S. patent application Ser. No. 09/436,119, filed Nov. 8, 1999, pursuant to a petition filed under 37 C.F.R. 1.53(c)(2)(i).

FIELD OF THE INVENTION

This invention relates to new N-(indolyl-cycloalkyl) azetidine derivatives which are useful as pharmaceuticals for the treatment of diseases caused by disorders of the serotonin-affected neurological systems, such as depression and anxiety.

BACKGROUND OF THE INVENTION

Pharmaceuticals which enhance serotonergic neurotransmission are useful for the treatment of many psychiatric disorders, including depression and anxiety. The first generation of non-selective serotonin-affecting drugs operated through a variety of physiological functions which endowed them with several side-effect liabilities. The more currently prescribed drugs, the selective serotonin (5-HT) reuptake inhibitors (SSRIs), act predominately by inhibiting 5-HT, which is released at the synapses, from being actively removed from the synaptic cleft via a presynaptic scrotonin transport carrier.

The present invention relates to a new class of molecules which have the ability to act at the 5-HT transporter. Such compounds are therefore potentially useful for the treatment of depression as well as other serotonin disorders.

Described in WO 95/20588 are compounds of general formula:

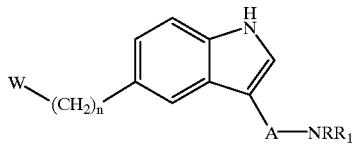

Wherein R and $R_1$ are each independently hydrogen or $C_{1-4}$ alkyl, or R and $R_1$ are linked to form an azetidine ring. These compounds are reported to have activity at the $5HT_1$ receptor and be useful for the treatment of migraine, headache and headache associated with vascular disorder.

SUMMARY OF THE INVENTION

In accordance with this invention there is provided a group of compounds represented by the formula I:

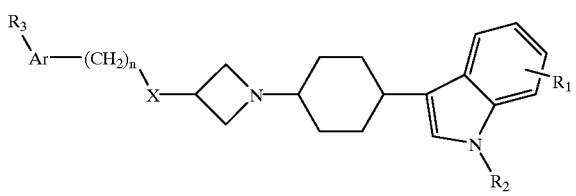

wherein:
X is N—R, O, $S(O)_m$;
m is an integer of 0 to 2;
n is an integer of 0 to 4;

Ar is an aryl group of 6 to 12 carbon atoms optionally substituted with 1 to 3 groups selected independently from $R_3$, $R_4$ and $R_5$, or a heteroaryl group of 4 to 10 carbon atoms optionally substituted with 1 to 3 selected independently from $R_3$, $R_4$ and $R_5$;

R and $R_2$ are independently H, straight chain alkyl of 1 to 6 carbon atoms, branched alkyl of 3 to 6 carbon atoms, cycloalkyl of 3 to 6 carbon atoms, alkoxycarbonyl of 1 to 6 carbon atoms, alkylcarbonyl of 1 to 6 carbon atoms, aminocarbonyl, or alkylaminocarbonyl of 1 to 4 carbon atoms;

$R_1$, $R_3$, $R_4$ and $R_5$ are independently H, straight chain alkyl of 1 to 4 carbon atoms, branched alkyl of 3 to 6 carbon atoms, cycloalkyl of 3 to 8 carbon atoms, halogen, alkoxy group of 1 to 4 carbon atoms, haloalkyl of 1 to 4 carbon atoms, hydroxy, nitro, amino, sulfonyl, cyano, carboxy, alkoxycarbonyl of 1 to 4 carbon atoms, alkylcarbonyl of 1 to 4 carbon atoms, aminocarbonyl, or alkylaminocarbonyl of 1 to 4 carbon atoms;

and all crystalline forms or a pharmaceutically acceptable salt thereof.

In a preferred aspect of this invention are provided compounds of formula I wherein:

X is O, or NR;
n is an integer of 0 to 1;
Ar is an aryl group of 6 to 10 carbon atoms optionally substituted with 1 to 3 groups selected independently from $R_3$, $R_4$ and $R_5$, or a heteroaryl group of 5 to 10 carbon atoms optionally substituted with 1 to 3 groups selected independently from $R_3$, $R_4$ and $R_5$;

R and $R_2$ are independently H, straight chain alkyl of 1 to 6 carbon atoms, branched alkyl of 3 to 6 carbon atoms, or cycloalkyl of 3 to 6 carbon atoms;

$R_1$, $R_3$, $R_4$ and $R_5$ are independently H, straight chain alkyl of 1 to 6 carbon atoms, branched alkyl of 3 to 6 carbon atoms, cycloalkyl of 3 to 6 carbon atoms, halogen, alkoxy of 1 to 4 carbon atoms, haloalkyl of 1 to 4 carbon atoms, hydroxy, nitro, nitrile, amino, sulfonyl, cyano, carboxy, alkoxycarbonyl of 1 to 4 carbon atoms, alkylcarbonyl of 1 to 4 carbon atoms, aminocarbonyl, or alkylaminocarbonyl of 1 to 4 carbon atoms;

and all crystalline forms or a pharmaceutically acceptable salt thereof.

In another preferred group of compounds of this invention:

X is $S(O)_m$;
m is an integer of 0 to 2;
n is an integer of 0 or 1;
Ar is an aryl group of 6 to 10 carbon atoms optionally substituted with 1 to 3 groups selected independently from $R_3$, $R_4$ and $R_5$, or a heteroaryl group of 5 to 10 carbon atoms optionally substituted with 1 to 3 groups selected independently from $R_3$, $R_4$ and $R_5$;

R and $R_2$ are independently H, straight chain alkyl of 1 to 6 carbon atoms, branched alkyl of 3 to 6 carbon atoms, or cycloalkyl of 3 to 6 carbon atoms;

$R_1$, $R_3$, $R_4$ and $R_5$ are independently selected from H, straight chain alkyl of 1 to 6 carbon atoms, branched alkyl of 3 to 6 carbon atoms, cycloalkyl of 3 to 6 carbon atoms, halogen, alkoxy of 1 to 4 carbon atoms, haloalkyl of 1 to 4 carbon atoms, hydroxy, nitro, nitrile, amino, sulfonyl, cyano, carboxy, alkoxycarbonyl of 1 to 4 carbon atoms, alkylcarbonyl of 1 to 4 carbon atoms, aminocarbonyl, or alkylaminocarbonyl of 1 to 4 carbon atoms;

and all crystalline forms or a pharmaceutically acceptable salt thereof.

A subset of these preferred compounds includes those in which X is S(O)$_m$; m is an integer from 0 to 2; and Ar is a phenyl ring optionally substituted by from 1 to 3 groups independently selected from $R_3$, $R_4$ and $R_5$, defined above.

Aryl, as used herein refers to single or multiple 6 to 12 membered aromatic ring radicals including but not limited to phenyl, naphthalene, anthracene, phenanthrene, indene and indacene, in some embodiments of the present invention, the aryl group may be substituted with one to three groups selected from $R_3$, $R_4$ and $R_5$.

Heteroaryl as used herein refers to single or multiple 5 to 10 membered aromatic ring radicals having from 1 to 3 hetero atoms independently selected from nitrogen, oxygen and sulfur, including, but not limited to, furan, thiophene, pyrrole, imidazole, oxazole, thiazole, isoxazole, pyrazole, isothiazole, oxadiazole, triazole, thiadiazole, quinolizine, quinoline, isoquinoline, cinnoline, phthalazine, quinazoline, quinoxaline, napthyridine, pteridine, pyridine, pyrazine, pyrimidine, pyridazine, pyran, triazine, indole, isoindole, indazole, indolizine, and isobenzofuran. In some embodiments of the present invention, the heteroaryl group is substituted with one to three groups selected from those of $R_3$, $R_4$ and $R_5$.

Alkyl, whether used alone or as part of another group includes straight and branched chain alkyl groups containing from 1 to 6 carbon atoms, for example, methyl, ethyl, propyl, isopropyl, butyl, i-butyl and t-butyl are encompassed by the term alkyl. In alkyl-containing groups herein, such as alkylcarbonyl and alkylaminocarbonyl groups, the number of carbon atoms listed refers to the alkyl group, itself, and not including the carbonyl carbon. In some embodiments of the present invention alkyl may refer to substituted or unsubstituted alkyl. The substituted alkyl groups in these compounds may be fully substituted, such as with perhalogenated compounds. Other alkyl groups in these definitions may be substituted by from 1 to 3 substituents selected from halogen, hydroxy, CN, $NO_2$, or $NH_3$. The number of carbon number refers to carbon backbone and does not include carbon atoms of substituents such as alkoxy substitutions and the like.

Among the most preferred compounds of the present invention are:

{1-[cis-4-(5-Fluoro-1H-indol-3-yl)-cyclohexyl]-azetidin-3-yl)-2-methoxy-phenyl)amine;

{1-[trans-4-(5-fluoro-1H-indol-3-yl)-cyclohexyl]-azetidin-3-yl)-2-methoxy-phenyl)amine;

3-{cis-4-[3-(3-fluoro-phenoxy)-azetidin-1-yl]-cyclohexyl}-1H-indole-5 carbonitrile;

3-{trans-4-[3-(3-fluoro-phenoxy)-azetidin-1-yl]-cyclohexyl}-1H-indole-5-carbonitrile;

2-{cis-4-[3-(3-methoxy-phenoxy)-azetidin-1-yl]-cyclohexyl}-1H-indole-5-carbonitrile;

2-{trans-4-[3-(3-methoxy-phenoxy)-azetidin-1-yl]-cyclohexyl}-1H-indole-5-;

{1-[cis-4-(5-fluoro-1H-indol-3-yl)-cyclohexyl]-azetidin-3-yl}-(3-fluoro-phenyl)-amine;

{1-[cis-4-(1H-indol-3-yl)-cyclohexyl]-azetidin-3-yl}-(2-methoxy-phenyl)-amine;

{1-[trans-4-(1H-indol-3-yl)-cyclohexyl]-azetidin-3-yl}-(2-methoxy-phenyl)-amine;

2-{cis-4-[3-(3-methoxy-phenoxy)-azetidin-1-yl]-cyclohexyl}-1H-indole;

2-{trans-4-[3-(3-methoxy-phenoxy)-azetidin-1-yl]-cyclohexyl}-1H-indole;

5-fluoro-3-{cis-4-[3-(3-fluoro-phenoxy)-azetidin-1-yl]-cyclohexyl}-1H-indole;

5-fluoro-3-{trans-4-[3-(3-fluoro-phenoxy)-azetidin-1-yl]-cyclohexyl}-1H-indole;

5-fluoro-3-{cis-4-[3-(3-methoxy-phenoxy)-azetidin-1-yl]-cyclohexyl}-1H-indole;

5-fluoro-3-{trans-4-[3-(3-methoxy-phenoxy)-azetidin-1-yl]-cyclohexyl}-1H-indole;

3-{cis-4-[3-(3-fluoro-phenoxy)-azetidin-1-yl]-cyclohexyl}-1H-indole;

3-{trans-4-[3-(3-fluoro-phenoxy)-azetidin-1-yl]-cyclohexyl}-1H-indole;

6-fluoro-3-{cis-4-[3-(3-fluoro-phenoxy)-azetidin-1-yl]-cyclohexyl}-1H-indole;

6-fluoro-3-{trans-4-[3-(3-fluoro-phenoxy)-azetidin-1-yl]-cyclohexyl}-1H-indol;

or a pharmaceutically acceptable salt of one or more of these compounds.

It is understood that the definition of the compounds of formula I, when R, $R_1$, $R_2$ or $R_3$ contain asymmetric carbons, encompass all possible stereoisomers and mixtures thereof which possess the activity discussed below. In particular, it encompasses racemic modifications and any optical isomers which possess the indicated activity. Optical isomers may be obtained in pure form by standard separation techniques.

Pharmaceutically acceptable salts are those derived from such organic and inorganic acids as: lactic, citric, acetic, tartaric, succinic, maleic, malonic, oxalic, fumaric, hydrochloric, hydrobromic, phosphoric, nitric, sulfuric, methanesulfonic, and similarly known acceptable acids. Where R, $R_1$, $R_2$ or $R_3$ contain a carboxyl group, salts of the compounds of this invention may be formed with bases such as alkali metals (Na, K, Li) or the alkaline earth metals (Ca or Mg).

As mentioned previously, the compounds of formula I have been found to have affinity for the 5-HT reuptake transporter. They are therefore useful in the treatment of diseases affected by disorders of the serotonin affected neurological systems, such as depression, anxiety, sleep disorders, sexual dysfunction, alcohol and cocaine addiction, cognition enhancement and related problems. The present invention accordingly provides methods of treatment or prevention of these maladies, the methods comprising administering to a mammal, preferably a human, in need thereof pharmaceutically effective amount of a compound of this invention, or a pharmaceutically acceptable salt thereof.

This invention also provides pharmaceutical compositions which comprise one or more compounds of this invention, or a pharmaceutically acceptable salt thereof, in combination or association with one or more pharmaceutically acceptable carriers or excipients. The compositions are preferably adapted for oral or subcutaneous administration. However, they may be adapted for other modes of administration.

The compositions of the invention may be formulated with conventional excipients, such as a filler, a disintegrating agent, a binder, a lubricant, a flavoring agent and the like. They are formulated in conventional manner, for example, in a manner similar to that use for known antihypertensive agents, diuretics and β-blocking agents.

Applicable solid carriers or excipients can include one or more substances which may also act as flavoring agents, lubricants, solubilizers, suspending agents, fillers, glidants, compression aids, binders or tablet-disintergrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

In order to obtain consistency of administration, it is preferred that a composition of the invention is in the form of a pharmaceutically effective unit dose. Suitable unit dose forms include tablets, capsules and powders in sachets or vials. Such unit dose forms may contain from 0.1 to 100 mg of a compound of the invention and preferably from 2 to 50 mg. Still further preferred unit dosage forms contain 5 to 25 mg of a compound of the present invention. The compounds of the present invention can be administered orally at a dose range of about 0.01 to 100 mg/kg or preferably at a dose range of 0.1 to 10 mg/kg. Such compositions may be administered from 1 to 6 times a day, more usually from 1 to 4 times a day.

The following specific examples illustrate the synthetic procedures for the preparation of intermediates and invention compounds and should not be construed as limiting the scope of this disclosure. Those skilled in the art of organic synthesis may be aware of still other routes to prepare compounds of this invention. Reactants and intermediates are either commercially available or can be prepared according to standard literature procedures.

In accordance with the present invention, compounds of formula I may be prepared by Scheme I.

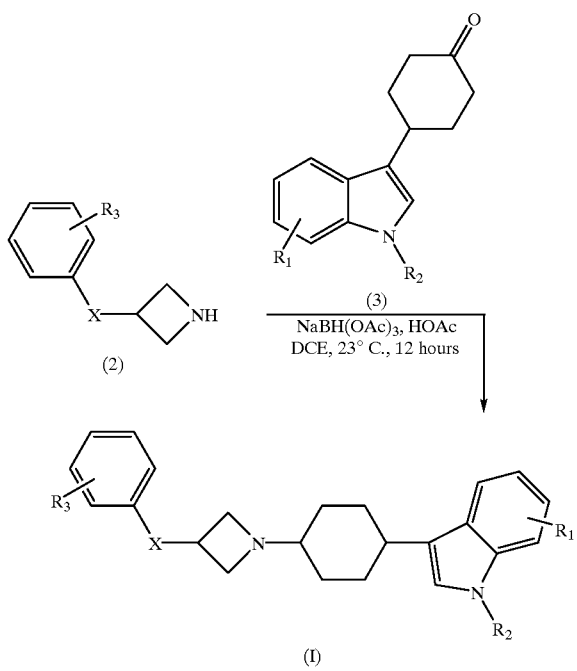

Scheme I

Thus, a compound of formula (2) is reacted with a compound of formula (3) in the presence of a reducing reagent such as sodium triacetoxyborohydride, and acetic acid in a solvent such as dichloroethane at 23° C. to give a compound of formula I in accordance with the procedure described by Abdel-Magid, Carson, Harris, Maryanoff and Shah in *J. Org. Chem.* 1996, 61, 3849.

In accordance with the present invention, compounds of formula (3) may be prepared by Scheme II.

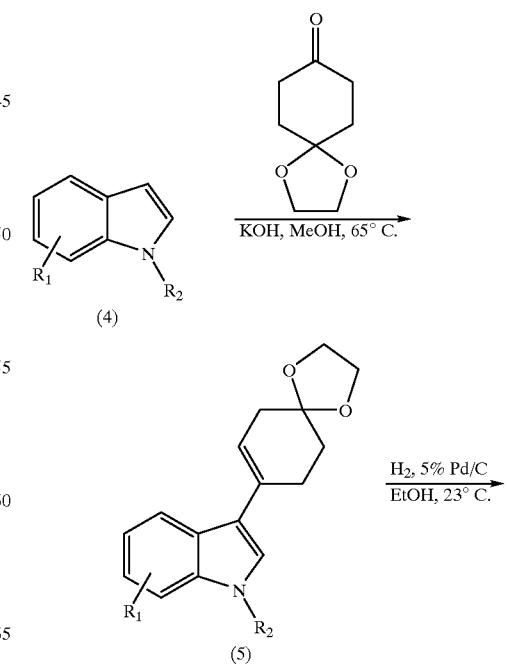

Scheme II

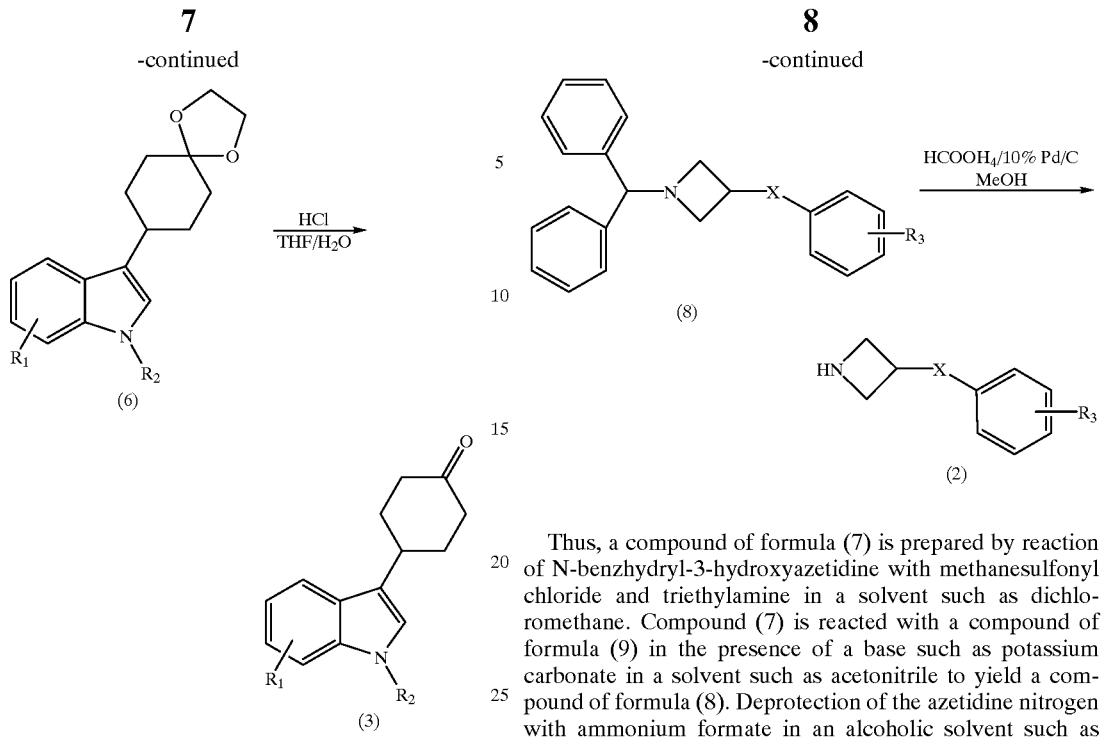

Thus a compound of formula (4) is reacted with 1,4-cyclohexanedione monoethylene ketal, potassium hydroxide in methanol at 65° C. to give compounds of formula (5) as described by Wustrow et al. in *J. Med. Chem.* 1997, 40, 250. Hydrogenation to a compound of formula (6) can be realized by treatment in suitable solvents such as an alcohol, but not limited to ethanol with $H_2$ and 5% Pd/C. Hydrolysis to a compound of formula (3) can be carried out using 1N HCl in a 1:1 mixture of THF and water.

In accordance with the present invention, compounds of formula (2) may be prepared by Scheme III.

Thus, a compound of formula (7) is prepared by reaction of N-benzhydryl-3-hydroxyazetidine with methanesulfonyl chloride and triethylamine in a solvent such as dichloromethane. Compound (7) is reacted with a compound of formula (9) in the presence of a base such as potassium carbonate in a solvent such as acetonitrile to yield a compound of formula (8). Deprotection of the azetidine nitrogen with ammonium formate in an alcoholic solvent such as methanol yields a compound of formula (2).

Compounds of formula (2) where X is NR are prepared according to scheme IV. Standard N-alkylation methods may be used to convert a compound of formula (9) where R is hydrogen to a compound of formula (9) where R is alkyl.

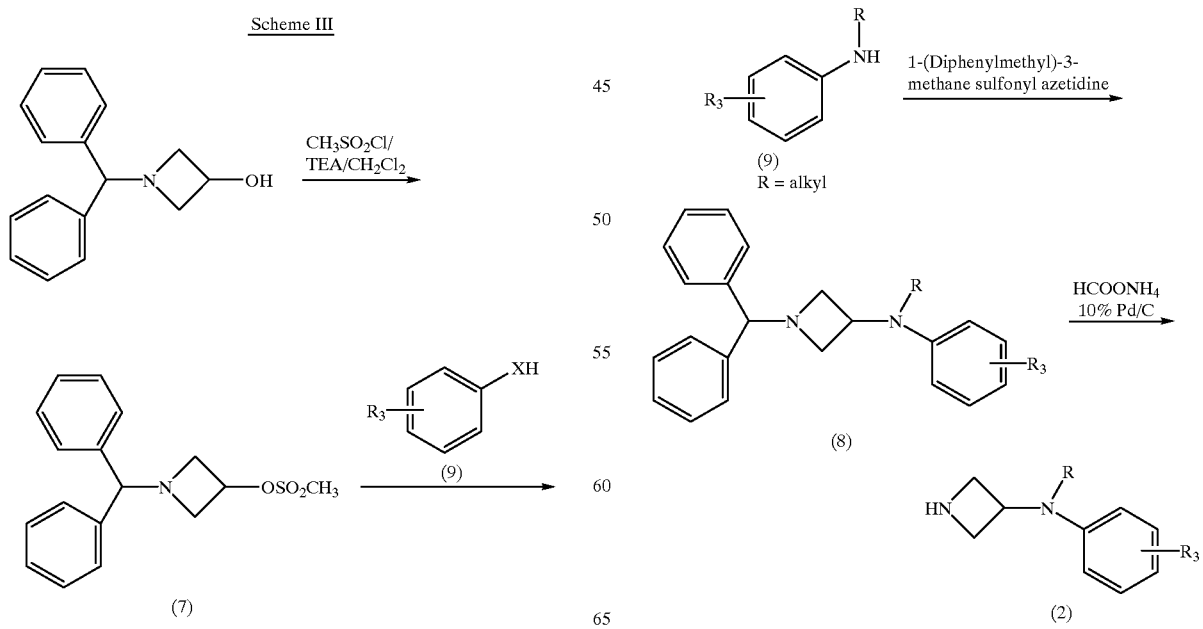

While the reaction schemes above show intermediates substituted only by $R_3$ groups, the presence of optional $R_4$ and $R_5$ groups in these compounds is understood.

The present invention further provides a compound of the invention for use as an active therapeutic substance. Compounds of formula I are of particular use in the treatment of diseases affected by disorders of the serotonin.

The present invention further provides a method of treating depression and anxiety in mammals including man, which comprises administering to the afflicted mammal an effective amount of a compound or a pharmaceutical composition of the invention.

The following examples are presented to illustrate rather than limit the present invention.

EXAMPLES

The 5-HT transporter affinity of the compounds of this invention was established in accordance with standard pharmaceutically accepted test procedures with representative compounds as follows:

Rat Brain $^3$H-Paroxetine Binding Assay (RB 5HT Transporter):

The following assay was used to determine a compound's affinity for the 5-HT transporter.

A protocol similar to that used by Cheetham et. al. (*Neuropharmacol.* 1993, 32, 737) was used. Briefly, frontal cortical membranes prepared from male S.D. rats were incubated with $^3$H-paroxetine (0.1 nM) for 60 min. at 25° C. All tubes also contained either vehicle, test compound (one to eight concentrations), or a saturating concentration of fluoxetine (10 μM) to define specific binding. All reactions are terminated by the addition of ice cold Tris buffer followed by rapid filtration using a Tom Tech filtration device to separate bound from free $^3$H-paroxetine. Bound radioactivity was quantitated using a Wallac 1205 Beta Plate® counter. Nonlinear regression analysis was used to determine $IC_{50}$ values which were converted to $K_i$ values using the method of Cheng and Prusoff (*Biochem. Pharmacol.* 1973, 22, 3099):

$$K_i = \frac{IC_{50}}{\text{Radioligand concentration}/(1 + KD)}$$

Inhibition of $^3$H-5-HT Uptake by cells Possessing the Human 5-HT Transporter (HC 5HT Transporter):

A human carcinoma cell line (Jar cells) possessing low endogenous levels of the 5-HT-transporter are seeded into 96 well plates and treated with staurosporine at least 18 h prior to assay. [Staurosporine greatly increases the expression of the 5-HT-transporter.] On the day of assay, vehicle, excess of fluoxetine, or test compound is added to various wells on the plate. All wells then receive $^3$H-5-HT and are incubated at 37° C. for 5 min. The wells are then washed with ice cold 50 mM Tris HCl (pH 7.4) buffer and aspirated to remove free $^3$H-5-HT. 25 μl of 0.25 M NaOH is then added to each well to lyse the cells and 75 μl scintillation cocktail (Microscint™ 20) added prior to quantitation on a Packard TopCount machine. Tubes with vehicle represent total possible uptake, radioactivity counted in tubes with fluoxetine represent nonspecific binding/uptake and is subtracted from the total possible uptake to give total possible specific uptake. This nonspecific binding (usual low in number) is then subtracted from the counts obtained in wells with various test compounds (or different concentrations of test drug) to give specific uptake in the presence of drug. Specific uptake is then expressed as a % of control values and is analyzed using nonlinear regression analysis (Prizm) to determine $IC_{50}$ values. If the compound is active at inhibiting 5-HT uptake, its counts will be close to that obtained with fluoxetine.

Results from these two assays are presented below in Table I.

TABLE I

| Compound | n | RB 5HT Transporter $K_i$ (nM) | HC 5HT Transporter $IC_{50}$ (nM) |
|---|---|---|---|
| Example 1a | 1 | 15.0 | 962 |
| Example 1b | 1 | 17.0 | 591 |
| Example 2a | 1 | 16.0 | 336.50 |
| Example 2b | 1 | 48.0 | 282 |
| Example 3a | 1 | 2.38 | 91 |
| Example 3b | 1 | 11.0 | 232 |
| Example 4 | 1 | 18.0 | 6390 |
| Example 5a | 1 | 124 | — |
| Example 5b | 1 | 34.0 | — |
| Example 6a | 1 | 120.0 | — |
| Example 6b | 1 | — | — |
| Example 7a | 1 | 257 | — |
| Example 7b | 1 | 68 | 6000 |
| Example 8a | 1 | 24.0 | 6000 |
| Example 8b | 1 | 45.0 | 1500 |
| Example 9a | 1 | 275.0 | — |
| Example 9b | 1 | 455.0 | — |
| Example 10a | 1 | 190 | — |
| Example 10b | 1 | 73 | 4600 |

Example 1a

{1-[cis-4-(5-Fluoro-1H-indol-3-yl)-cyclohexyl]-azetidin-3-yl)-2-methoxy-phenyl)-amine

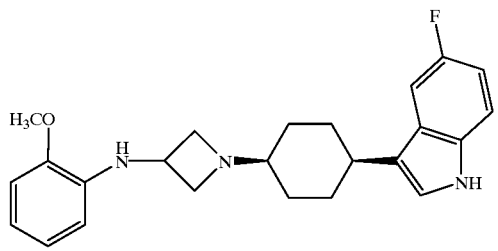

Step 1

4-(5-Fluoro-1H-3-indolyl)-cyclohex-3-ene-ethylene ketal

5-Fluoroindole (4.96, 0.036 mol), 1,4-cyclohexanedione monoethylene ketal (7.17 g, 0.046 mol) and potassium hydroxide (6 g, 0.043 mol) were heated to reflux in 70 mL of methanol for 6 h. The reaction was cooled and the product was isolated by filtration and washed with water to give 8.59 g (86%) of product as a white solid: mp 153–155° C.

Step 2

4-(5-Fluoro-1H-3-indolyl)-cyclohexanone ethylene ketal

A mixture of 4-(5-fluoro-1H-3-indolyl)-cyclohex-3-en-ethylene ketal (8.5 g) and 10% palladium on carbon (2.72 g) in ethanol (200 mL) was hydrogenated for 5 h. The catalyst was filtered off and the solvent was removed under vacuum. Chromatography (methanol-methylene chloride) afforded 7.55 g (82%) of product as a white solid: mp 183–185° C.

Step 3

4-(5-Fluoro-1H-3-indolyl)-cyclohexanone

A solution of 4-(5-fluoro-1H-3-indolyl)-cyclohexanone ethylene ketal (2.8 g, 10 mmol) in 2 L of 1:1 tetrahydrofuran-hydrochloric acid (1N) was allowed to stir at room temperature for 16 h. The solvent was evaporated under vacuum. The crude product was dissolved in ethyl acetate, washed with 1N sodium hydroxide (3×150 mL). The organic layer was dried over anhydrous sodium sulfate, and filtered. Chromatography (40% ethyl acetate/hexanes) afforded 2.1 g (91%) of product as a yellow solid: mp 112–114° C.

Step 4

1-(Diphenylmethyl)-3-methane sulfonyl azetidine

To a cold solution of 34 g (0.142 mol) of 1-(diphenylmethyl)-3-hydroxyazetidine in 200 mL of $CH_2Cl_2$ was added 30 mL (212 mol) of triethylamine. To the cold mixture a solution of 19.5 g (0.171 mol) of methane-sulfonyl chloride in 50 mL of $CH_2Cl_2$ was added dropwise. The reaction was stirred at room temperature for 2 h. Water was added and the methylene chloride was removed under vacuo. The product was extracted with ether, the combined extracts were dried over anhydrous sodium sulfate, and filtered to yield 36 g of product. $^1$H NMR (300 MHz, $CDCl_3$) δ 2.98 (s, 3H), 3.21 (m, 2H), 3.66 (m, 2H), 4.39 (s, 3H), 5.10 (m, 1H), 7.22 (m, 2H), 7.27 (m, 4H), 7.38 (m, 4H).

Step 5

(1-Benzhydryl-azetidin-3-yl)-(2-methoxy-phenyl)-amine

To a solution of 4.1 g (0.033 mol) of o-anisidine in 20 mL DMF, 4.6 g (0.033 mol) of $K_2CO_3$ was added, followed by 9.5 g (0.030 mol) of 1-(diphenylmethyl)-3-methane sulfonyl azetidine. The reaction was heated at 80° C. for 5 h. Water was added and the product was extracted with ether. The organic phase was dried and the solvent was removed under vacuo. The residue was filtered through silica gel, starting with 100% methylene chloride, then 25% ethyl acetate/hexane to give 1.5 g of the desired product: mp 75–77° C. $^1$H NMR (300 MHz, $CDCl_3$) δ 2.89 (dd, 2H), 3.70 (dd, 2H), 3.84 (s, 3H), 4.13 (m, 1H), 4.40 (m, 1H), 4.38 (s,1H), 6.42 (dd,1H), 6.69 (dd, 1H), 6.79 (m, 2H), 7.20 (m, 2H), 7.26 (m, 4H), 7.42 (m, 4H); MS (ES) m/z (relative intensity): 345 ($M^+$+H).

Elemental analysis for $C_{23}H_{24}N_2O$
Calculated: C, 80.20; H, 7.02; N, 8.13
Found: C, 80.53; H, 7.17; N, 8.13.

Step 6

Azetidin-3-yl-(2-methoxy-phenyl-amine)

A solution of 2.0 g of (1-benzhydryl-azetidin-3-yl)-(2-methoxyphenyl)-amine in 30 mL of methanol was added to a suspension of 10% Pd/C in methanol. 4.0 g of ammonium formate was added portion wise and the reaction was heated under reflux for 2 h. The mixture was cooled, filtered over celite, the filtrate was evaporated. The residue was triturated with $CH_2Cl_2$, and filtered. The filtrate was evaporated to give 0.840 g of the desired product.

Step 7

{1-[cis-4-(5-Fluoro-1H-indol-3-yl)-cyclohexyl]-azetidin-3-yl)-2-methoxy-phenyl)-amine To a solution of 0.170 g of (1-benzhydryl-azetidin-3-yl)-(2-methoxy-phenyl)-amine in 10 mL of $CH_2Cl_2$, was added 4-(5-fluoro-1-H-3-indolyl)-cyclohexanone followed by 0.420 g of sodium triacetoxyborohydride. The reaction was stirred at room temperature overnight. It was quenched with 1N NaOH, and the product was extracted with ether. The organic phase was washed with water and dried over magnesium sulfate. The product was filtered through 150 mL of silica gel using 50% ethyl acetate/hexanes, 75% ethyl acetate/hexanes, and finally 100% ethyl acetate to give 0.150 g of the desired product: mp 158–160° C. $^1$H NMR (300 MHz, $CDCl_3$) δ 1.50–1.94 (m, 8H), 2.28 (m, 1H), 2.84–2.90 (m, 2H), 3.80–3.85 (m, 5H), 4.08–4.14 (m, 1H), 4.38 (m, 1H), 6.51–6.68 (dd, 1H), 6.69–6.91 (m, 4H), 7.07 (d, 1H), 7.24–7.28 (m, 2H), 8.02 (s, 1H); MS (ES) m/z (relative intensity): 394 ($M^+$+H).

Example 1b

{1-[trans-4-(5-Fluoro-1H-indol-3-yl)-cyclohexyl]-azetidin-3-yl)-2-methoxy-phenyl)-amine

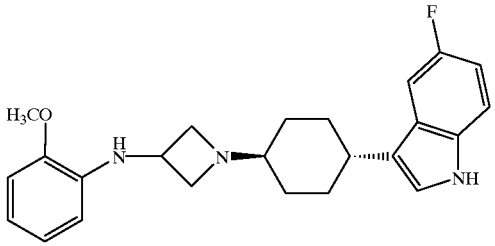

The trans isomer of the compound of Example 1a was isolated at the same time as the cis isomer as an off white solid (0.045 g): mp 73–76° C. MS (ES) m/z (relative intensity): 394 ($M^+$+H).

Example 2a 3-(cis-4-[3-(3-Fluoro-phenoxy)-azetidin-1-yl]-cyclohexyl)-1H-indole-5-carbonitrile

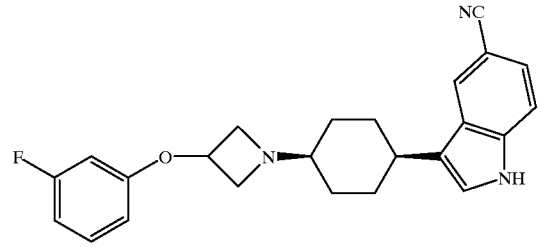

Step 1

4-(5-Cyano-1H-3-indolyl)-cyclohex-3-ene-ethylene ketal

The title compound was prepared according to the procedure of Example 1a, Step 1 except that 5-cyanoindole was used in place of 5-fluoroindole. Yield: 50%; mp 158–160° C.

Step 2

4-(5-Cyano-1H-3-indolyl)-cyclohexanone ethylene ketal

The title compound was prepared according to the procedure of Example 1a, Step 2, using 4-(5-cyano-1H-3-indolyl)-cyclohex-3-ene-ethylene ketal. Yield: 95%; mp 153–155° C.

Step 3

3-(4-Oxo-cyclohexyl)-1H-indole-5-carbonitrile

The title compound was prepared according to the procedure of Example 1, Step 3, except that 4-(5-cyano-1H-3-indolyl)-cyclohexanone ethylene ketal was used. Yield: 81%; mp 162–164° C.

Step 4

1-Benzhydryl-3-(3-Fluoro-phenoxy)-azetidine

To a solution of 3.9 g (0.035 mol) of 3-fluorophenol in 250 mL of acetonitrile, was added 6.3 g (0.045 mol) of $K_2CO_3$ followed by 12.25 g (0.039 mol) of 1-(diphenylmethyl)-3-methane sulfonyl azetidine, prepared according to the procedure of Example 1a, Step 4. The reaction mixture was heated at 75° C. for 18 h. The solvent was removed under vacuo, and the residue was taken up in a mixture of ether and water. The aqueous layer was extracted with ether, the combined extracts were dried over magnesium sulfate, and the solvent was removed under vacuo. The product was filtered through 500 mL of silica gel, eluted with 50% $CH_2Cl_2$/hexane then 15% ethyl acetate/hexane to give 3.4 g of the title compound: mp 81–82° C. $^1H$ NMR (300 MHz, $CDCl_3$) δ 3.17 (dd, 2H), 3.72 (dd, 2H), 4.46 (s, 1H), 4.77 (m, 1H), 6.48 (dd, 1H), 6.53 (dd, 1H), 6.63 (m, 1H), 7.22 (m, 3H), 7.29 (m, 4H), 7.31 (dd, 4H); MS (ES) m/z (relative intensity): 334 ($M^+$+H).

Step 6

3-(3-Fluoro-phenoxy)-azetidine

A solution of 2.50 g of 1-benzhydryl-3-(3-fluoro-phenoxy)-azetidine in 10 mL of THF was added to a suspension of 10% Pd/C in methanol. Ammonium formate (4.6 g) were added portion wise and the reaction was heated under reflux for 3 h. The mixture was cooled, filtered through celite, and the filtrate was concentrated. The residue was triturated with $CH_2Cl_2$ and filtered. The filtrate was concentrated to give 0.840 g of the desired product.

Step 7

3-(cis-4-[3-(3-Fluoro-phenoxy)-azetidin-1-yl]-cyclohexyl)-1H-indole-5-carbonitrile To a solution of 0.170 g of 3-(3-fluoro-phenoxy)-azetidine in 10 mL of $CH_2Cl_2$ was added 0.180 g of 3-(4-oxo-cyclohexyl)-1H-indole-5-carbonitrile followed by 0.420 g of sodium triacetoxyborohydride. The reaction was stirred at room temperature overnight. It was quenched with 1N NaOH and the product was extracted with ether. The organic phase was washed with water, dried over magnesium sulfate, filtered, and concentrated. The product was filtered through 150 mL of silica gel using 50% ethyl acetate/hexane, 75% ethyl acetate/hexane and finally 100% ethyl acetate to give 0.095 g of the desired product: mp 187–190° C. $^1H$ NMR (300 MHz, $CDCl_3$) δ 1.51–1.65 (m, 2H), 1.69–1.75 (m, 4H), 1.77–1.90 (m, 2H), 2.45 (m, 1H), 2.90 (m, 1H), 3.03 (dd, 2H), 3.81 (dd, 2H), 4.77 (m, 1H), 6.53–6.59 (m, 2H), 6.66 (m, 1H), 7.13–7.22 (m, 2H), 7.39 (dd, 2H), 8.00 (s, 1H), 8.28 (s, 1H); MS (ES) m/z (relative intensity): 390 ($M^+$+H).

Elemental analysis for $C_{24}H_{24}FN_3O$

Calculated: C, 74.01; H, 6.21; N, 10.79

Found: C, 73.95; H, 6.24; N, 10.45.

Example 2b

3-(trans-4-[3-(3-Fluoro-phenoxy)-azetidin-1-yl]-cyclohexyl)-1H-indole-5-carbonitrile

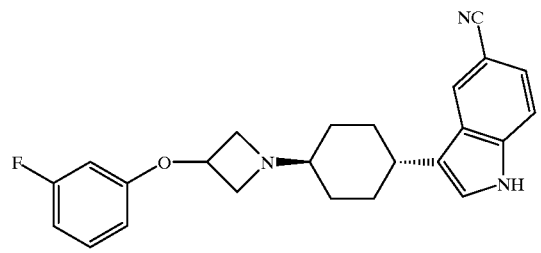

The trans isomer of the compound of Example 2a was isolated at the same time as the cis isomer as a white solid (0.037 g): mp 186–192° C. $^1H$ NMR (300 MHz, $CDCl_3$) δ 1.98–1.33 (m, 2H), 1.45–1.49 (m, 2H), 1.95–1.99 (m, 2H), 2.14–2.23 (m, 3H), 2.73–2.83 (m,1H), 3.17 (dd, 2H), 3.89 (dd, 2H), 4.78 (m, 1H), 6.48–6.70 (m, 3H), 7.06 (d, 1H), 7.18–7.24 (m, 2H), 7.40 (dd, 2H), 8.00 (s, 1H), 8.23 (s, 1H); MS (ES) m/z (relative intensity): 390 ($M^+$+H).

Example 3a

2-{cis-4-[3-(3-Methoxy-phenoxy)-azetidin-1-yl]-cyclohexyl}-1H-indole-5-carbonitrile

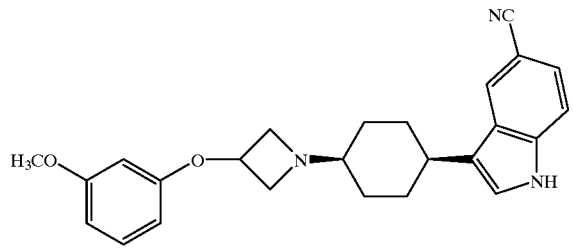

The title compound was prepared according to the procedure of Example 2a, using m-methoxy-phenol in Step 5, and 3-(4-oxo-cyclohexyl)-1H-indole-5-carbonitrile in Step 7. mp 126–127° C. MS (ES) m/z (relative intensity): 402 ($M^+$+H).

Example 3b

2-{trans-4-[3-(3-Methoxy-phenoxy)-azetidin-1-yl]-cyclohexyl}-1H-indole-5-carbonitrile

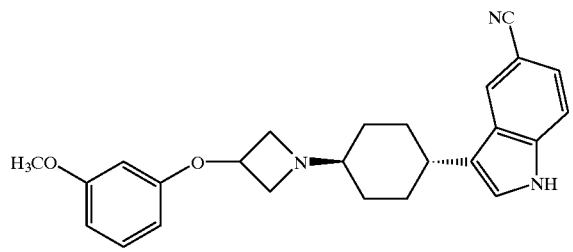

The trans isomer of the compound of Example 3a was isolated at the same time as the cis isomer as a white solid (0.055 g ): mp 58–62° C. MS (ES) m/z (relative intensity): 402 ($M^+$+H).

Example 4

{1-[cis-4-(5-Fluoro-1H-indol-3-yl)-cyclohexyl]-azetidin-3-yl}-(3-fluoro-phenyl)-amine

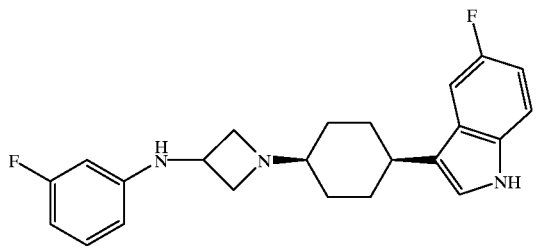

The title compound was prepared according to the procedure of Example 1a, Step 5 using m-fluoroaniline: mp 67–70° C. MS (ES) m/z (relative intensity): 382 (M$^+$+H).

Example 5a

{1-[cis-4-(1H-Indol-3-yl)-cyclohexyl]-azetidin-3-yl}-(2-methoxy-phenyl)-amine

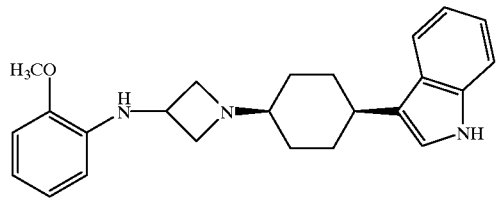

The title compound was prepared according to the procedure of Example 1a, using 3-(4-oxo-cyclohexyl)-1H-indole in Step 7: mp 67–70° C. MS (ES) m/z (relative intensity): 382 (M$^+$+H).

Example 5b

{1-[trans-4-(1H-Indol-3-yl)-cyclohexyl]-azetidin-3-yl}-(2-methoxy-phenyl)-amine

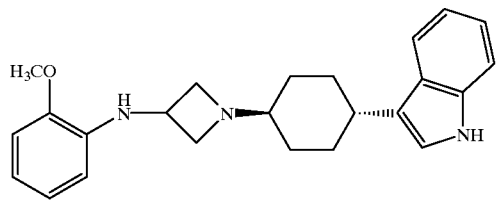

The trans isomer of the compound of Example 5a was isolated at the same time as the cis isomer as an off white solid (0.045 g): mp 73–76° C. MS (ES) m/z (relative intensity): 394 (M$^+$+H).

Example 6a

2-{cis-4-[3-(3-Methoxy-phenoxy)-azetidin-1-yl]-cyclohexyl}-1H-indole

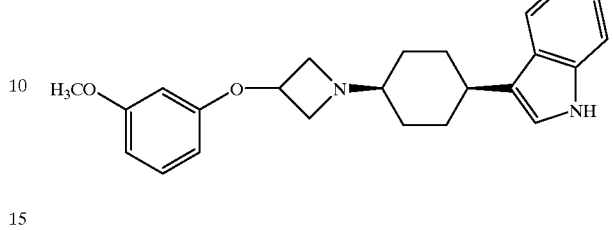

The title compound was prepared according to the procedure of Example 2a, using m-methoxy-phenol in Step 5, and 3-(4-oxo-cyclohexyl)-1H-indole in Step 7: mp 126–127° C. MS (ES) m/z (relative intensity): 383 (M$^+$+H).

Elemental analysis for $C_{23}H_{24}F_2N_2O_2$

Calculated: C, 72.23; H, 6.33; N, 7.32

Found: C, 72.43; H, 5.88; N, 7.07.

Example 6b

2-{trans-4-[3-(3-Methoxy-phenoxy)-azetidin-1-yl]-cyclohexyl}-1H-indole

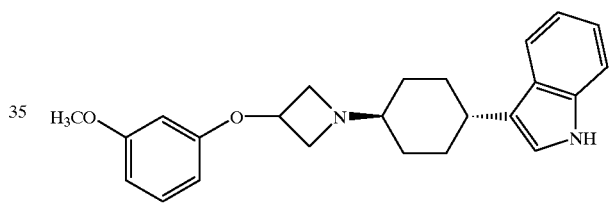

The trans isomer of the compound of Example 6a was isolated at the same time as the cis isomer as an off white solid: mp 52–57° C. MS (ES) m/z (relative intensity): 383 (M$^+$+H).

Example 7a

5-Fluoro-3-{cis-4-[3-(3-fluoro-phenoxy)-azetidin-1-yl]-cyclohexyl}-1H-indole

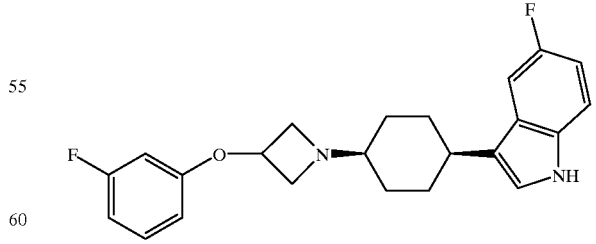

The title compound was prepared according to the procedure of Example 2a, Step 7 using 4-(5-fluoro-1H-3-indolyl)-cyclohexanone: mp 119–125° C. MS (ES) m/z (relative intensity): 383 (M$^+$+H).

Example 7b

5-Fluoro-3-{trans-4-[3-(3-fluoro-phenoxy)-azetidin-1-yl]-cyclohexyl}-1H-indole

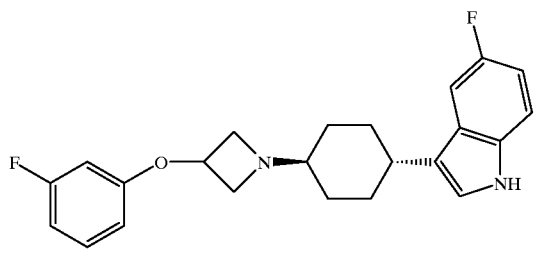

The trans isomer of the compound of Example 7a was isolated at the same time as the cis isomer as an off white solid: mp 52–57° C. MS (ES) m/z (relative intensity): 395 ($M^+$+H).

Example 8a

5-Fluoro-3-{cis-4-[3-(3-methoxy-phenoxy)-azetidin-1-yl]-cyclohexyl}-1H-indole

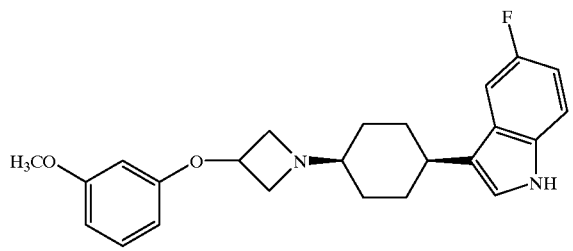

The title compound was prepared according to the procedure of Example 2a, using m-methoxy-phenol in Step 5, and 4-(5-fluoro-1H-3-indolyl)-cyclohexanone in Step 7: mp 125–127° C. MS (ES) m/z (relative intensity): 395 ($M^+$+H).

Example 8b

5-Fluoro-3-{trans-4-[3-(3-methoxy-phenoxy)-azetidin-1-yl]-cyclohexyl}-1H-indole

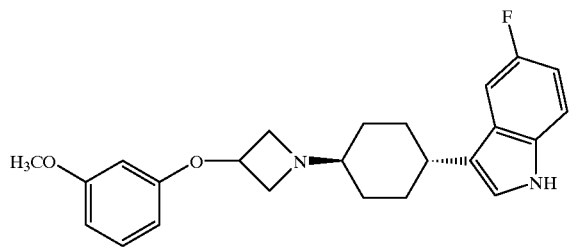

The trans isomer of the compound of Example 8a was isolated at the same time as the cis isomer as a white solid (0.055 g): mp 59–63° C. MS (ES) m/z (relative intensity): 395 ($M^+$+H).
Elemental analysis for $C_{24}H_{27}FN_2O_2$
   Calculated: C, 73.07; H, 6.90; N, 7.10
   Found: C, 72.98; H, 7.32; N, 6.51.

Example 9a

3-{4-[3-(3-Fluoro-phenoxy)-azetidin-1-yl]-cyclohexyl}-1H-indole

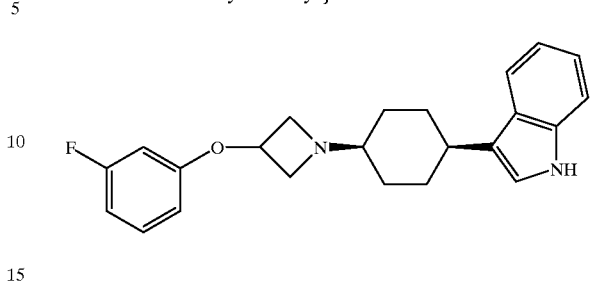

The title compound was prepared according to the procedure of Example 2a, usings 3-(4-oxo-cyclohexyl)-1H-indol in Step 7: mp 114–117° C. MS (ES) m/z (relative intensity): 365 ($M^+$+H).

Example 9b

3-{4-[3-(3-Fluoro-phenoxy)-azetidin-1-yl]-cyclohexyl}-1H-indole

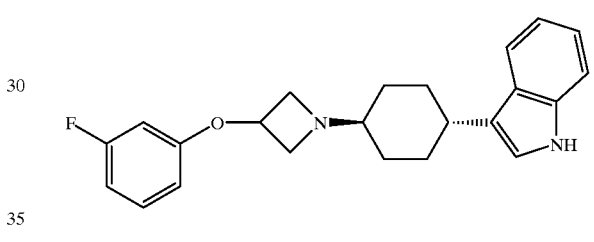

The tians isomer of the compound of Example 9a was isolated at the same time as the cis isomer as a white solid (0.055 g): mp 146–148° C. MS (ES) m/z (relative intensity): 365 ($M^+$+H).

Example 10a

6-Fluoro-3-{4-[3-(3-fluoro-phenoxy)-azetidin-1-yl]-cyclohexyl}-1H-indole

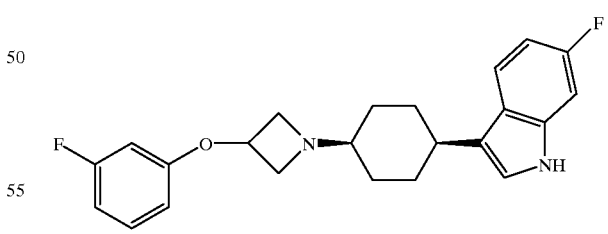

The title compound was prepared according to the procedure of Example 2a, using 4-(5-fluoro-1H-3-indolyl)-cyclohexanone in step 7: mp 117–123° C. MS (ES) m/z (relative intensity): 383 ($M^+$+H).
Elemental analysis for $C_{23}H_{24}F_2NO$
   Calculated: C, 72.23; H, 6.33; N, 7.32
   Found: C, 72.19; H, 6.49; N, 7.13.

Example 10b

6-Fluoro-3-{4-[3-(3-fluoro-phenoxy)-azetidin-1-yl]-cyclohexyl}-1H-indole

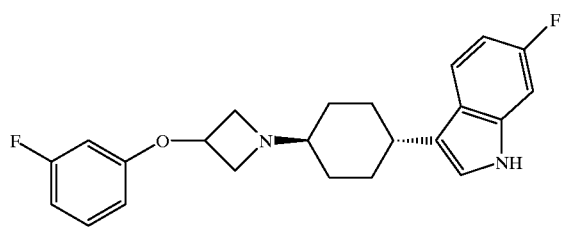

The trans isomer of the compound of Example 10a was isolated at the same time as the cis isomer as a white solid: mp 111–114° C. MS (ES) m/z (relative intensity): 383 (M$^+$+H).

Example 11

N-methyl o-Anisidine

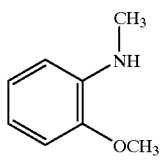

A solution of 12.3 g of o-anisidine in 50 mL of ethyl formate was heated under reflux for 6 h. Excess ethyl formate was removed under vacuo. The residue was washed with ether to cive 10.0 g of N-formyl o-anisidine.

To a cold solution of 9.0 g of N-formyl o-anisidine in 50 mL of THF was added 66 mL of a 1M solution of LAH in THF dropwise at 0° C. After complete addition the reaction mixture was stirred at 0° C. for one h. The reaction was then quenched with ethyl acetate, then with a saturated solution of NH$_4$Cl. The mixture was extracted with ether, the combined extracts were dried over magnesium sulfate, and the solvent was removed to give 6.0 g of product. $^1$H NMR (300 MHz, CDCl$_3$) δ 2.85 (s, 3H), 3.83 (s, 3H), 4.16 (s, 1H), 6.61 (dd, 1H), 6.69 (m, 1H), 6.75 (dd, 1H), 6.87 (m, 1H).

Example 12

(1-Benzhydryl-azetidin-3-yl)-(2-methoxy-phenyl)-methyl-amine

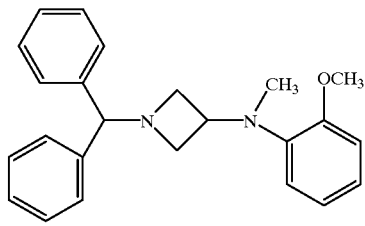

To a solution of 0.65 g of N-methyl o-anisidine in 15 mL of acetonitrile, was added 0.280 g of K$_2$CO$_3$, followed by 0.650 g of 1-(diphenylmethyl)-3-methane sulfonyl azetidine. The reaction mixture was heated at 80° C. for 1 h then at 50° C. overnight. Water was added and the mixture was extracted with ether. The organic phase was dried and the solvent was removed under vacuo. The product was filtered through 100 mL of silica gel, eluting a with 15% ethyl acetate/hexanes then 25% ethyl acetate/hexanes to give 0.200 g of the desired product: mp 91–95° C. MS (ES) m/z (relative intensity): 356 (M$^+$+H).

Elemental analysis for C$_{24}$H$_{26}$N$_2$O

Calculated: C, 80.41; H, 7.31; N, 7.81

Found: C, 80.57; H, 7.39; N, 7.69.

What is claimed:

1. A compound of the formula:

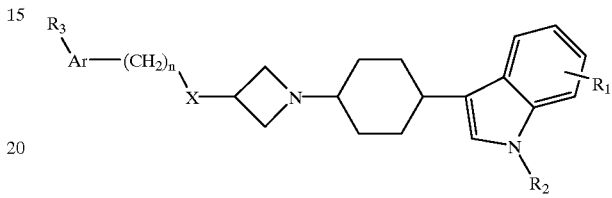

wherein:

X is N—R, O, S(O)$_m$;

m is an integer of 0 to 2;

n is an integer of 0 to 4;

Ar is an aryl group of 6 to 12 carbon atoms optionally substituted with 1 to 3 groups selected independently from R$_3$, R$_4$ and R$_5$, or a heteroaryl group of 4 to 10 carbon atoms optionally substituted with 1 to 3 groups selected independently from R$_3$, R$_4$ and R$_5$;

R and R$_2$ are independently H, straight chain alkyl of 1 to 6 carbon atoms, branched alkyl of 3 to 6 carbon atoms, cycloalkyl of 3 to 6 carbon atoms, alkoxycarbonyl of 1 to 6 carbon atoms, alkylcarbonyl of 1 to 6 carbon atoms, aminocarbonyl, or alkylaminocarbonyl of 1 to 4 carbon atoms;

R$_1$, R$_3$, R$_4$ and R$_5$ are independently H, straight chain alkyl of 1 to 4 carbon atoms, branched alkyl of 3 to 6 carbon atoms, cycloalkyl of 3 to 8 carbon atoms, halogen, alkoxy group of 1 to 4 carbon atoms, haloalkyl of 1 to 4 carbon atoms, hydroxy, nitro, amino, sulfonyl, cyano, carboxy, alkoxycarbonyl of 1 to 4 carbon atoms, alkylcarbonyl of 1 to 4 carbon atoms, aminocarbonyl, or alkylaminocarbonyl of 1 to 4 carbon atoms;

or a pharmaceutically acceptable salt thereof.

2. A compound of claim 1 wherein:

X is O, or NR;

n is an integer of 0 to 1;

Ar is an aryl group of 6 to 10 carbon atoms optionally substituted with 1 to 3 groups selected independently from R$_3$, R$_4$ and R$_5$, or a heteroaryl group of 5 to 10 carbon atoms optionally substituted with 1 to 3 groups selected independently from R$_3$, R$_4$ and R$_5$;

R and R$_2$ are independently H, straight chain alkyl of 1 to 6 carbon atoms, branched alkyl of 3 to 6 carbon atoms, or cycloalkyl of 3 to 6 carbon atoms;

R$_1$, R$_3$, R$_4$ and R$_5$ are independently H, straight chain alkyl of 1 to 6 carbon atoms, branched alkyl of 3 to 6 carbon atoms, cycloalkyl of 3 to 6 carbon atoms, halogen, alkoxy of 1 to 4 carbon atoms, haloalkyl of 1 to 4 carbon atoms, hydroxy, nitro, nitrile, amino, sulfonyl, cyano, carboxy, alkoxycarbonyl of 1 to 4 carbon atoms, alkylcarbonyl of 1 to 4 carbon atoms, aminocarbonyl, or alkylaminocarbonyl of 1 to 4 carbon atoms; or a pharmaceutically acceptable salt thereof.

3. A compound of claim 1 wherein:

X is S(O)$_m$;

m is an integer of 0 to 2;

n is an integer of 0 to 1;

Ar is an aryl group of 6 to 10 carbon atoms optionally substituted with 1 to 3 groups selected independently from $R_3$, $R_4$ and $R_5$, or a heteroaryl group of 5 to 10 carbon atoms optionally substituted with 1 to 3 groups selected independently from $R_3$, $R_4$ and $R_5$;

R and $R_2$ are independently H, straight chain alkyl of 1 to 6 carbon atoms, branched alkyl of 3 to 6 carbon atoms, or cycloalkyl of 3 to 6 carbon atoms;

$R_1$, $R_3$, $R_4$ and $R_5$ are independently H, straight chain alkyl of 1 to 6 carbon atoms, branched alkyl of 3 to 6 carbon atoms, cycloalkyl of 3 to 6 carbon atoms, halogen, alkoxy of 1 to 4 carbon atoms, haloalkyl of 1 to 4 carbon atoms, hydroxy, nitro, nitrile, amino, sulfonyl, cyano, carboxy, alkoxycarbonyl of 1 to 4 carbon atoms, alkylcarbonyl of 1 to 4 carbon atoms, aminocarbonyl, or alkylaminocarbonyl of 1 to 4 carbon atoms;

or a pharmaceutically acceptable salt thereof.

4. A compound of claim 1 which is {1-[cis-4-(5-Fluoro-1H-indol-3-yl)-cyclohexyl]-azetidin-3-yl)-2-methoxyphenyl)amine; or a pharmaceutically acceptable salt thereof.

5. A compound of claim 1 which is {1-[trans-4-(5-fluoro-1H-indol-3-yl)-cyclohexyl]-azetidin-3-yl)-2-methoxyphenyl)amine; or a pharmaceutically acceptable salt thereof.

6. A compound of claim 1 which is 3-{cis-4-[3-(3-fluoro-phenoxy)-azetidin-1-yl]-cyclohexyl}-1H-indole-5 carbonitrile; or a pharmaceutically acceptable salt thereof.

7. A compound of claim 1 which is 3-{trans-4-[3-(3-fluoro-phenoxy)-azetidin-1-yl]-cyclohexyl}-1H-indole-5-carbonitrile; or a pharmaceutically acceptable salt thereof.

8. A compound of claim 1 which is 2-{cis-4-[3-(3-methoxy-phenoxy)-azetidin-1-yl]-cyclohexyl}-1H-indole-5-carbonitrile; or a pharmaceutically acceptable salt thereof.

9. A compound of claim 1 which is 2-{trans-4-[3-(3-methoxy-phenoxy)-azetidin-1-yl]-cyclohexyl}-1H-indole-5-; or a pharmaceutically acceptable salt thereof.

10. A compound of claim 1 which is {1-[cis-4-(5-fluoro-1H-indol-3-yl)-cyclohexyl]-azetidin-3-yl}-(3-fluoro-phenyl)-amine; or a pharmaceutically acceptable salt thereof.

11. A compound of claim 1 which is {1-[cis-4-(1H-indol-3-yl)-cyclohexyl]-azetidin-3-yl}-(2-methoxy-phenyl)-amine; or a pharmaceutically acceptable salt thereof.

12. A compound of claim 1 which is {1-[trans-4-(1H-indol-3-yl)-cyclohexyl]-azetidin-3-yl}-(2-methoxy-phenyl)-amine; or a pharmaceutically acceptable salt thereof.

13. A compound of claim 1 which is 2-{cis-4-[3-(3-methoxy-phenoxy)-azetidin-1-yl]-cyclohexyl}-1H-indole; or a pharmaceutically acceptable salt thereof.

14. A compound of claim 1 which is 2-{trans-4-[3-(3-methoxy-phenoxy)-azetidin-1-yl]-cyclohexyl}-1H-indole; or a pharmaceutically acceptable salt thereof.

15. A compound of claim 1 which is 5-fluoro-3-{cis-4-[3-(3-fluoro-phenoxy)-azetidin-1-yl]-cyclohexyl}-1H-indole; or a pharmaceutically acceptable salt thereof.

16. A compound of claim 1 which is 5-fluoro-3-{trans-4-[3-(3-fluoro-phenoxy)-azetidin-1-yl]-cyclohexyl}-1H-indole; or a pharmaceutically acceptable salt thereof.

17. A compound of claim 1 which is 5-fluoro-3-{cis-4-[3-(3-methoxy-phenoxy)-azetidin-1-yl]-cyclohexyl}-1H-indole; or a pharmaceutically acceptable salt thereof.

18. A compound of claim 1 which is 5-fluoro-3-{trans-4-[3-(3-methoxy-phenoxy)-azetidin-1-yl]-cyclohexyl}-1H-indole.

19. A compound of claim 1 which is 3-{cis-4-[3-(3-fluoro-phenoxy)-azetidin-1-yl]-cyclohexyl}-1H-indole; or a pharmaceutically acceptable salt thereof.

20. A compound of claim 1 which is 3-{trans-4-[3-(3-fluoro-phenoxy)-azetidin-1-yl]-cyclohexyl}-1H-indole; or a pharmaceutically acceptable salt thereof.

21. A compound of claim 1 which is 6-fluoro-3-{cis-4-[3-(3-fluoro-phenoxy)-azetidin-1-yl]-cyclohexyl}-1H-indole; or a pharmaceutically acceptable salt thereof.

22. A compound of claim 1 which is 6-fluoro-3-{trans-4-[3-(3-fluoro-phenoxy)-azetidin-1-yl]-cyclohexyl}-1H-indol; or a pharmaceutically acceptable salt thereof.

23. A compound of the formula:

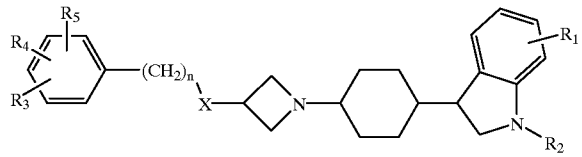

wherein:

X is N—R, O, S(O)$_m$;

m is an integer of 0 to 2;

n is an integer of 0 to 4;

R and $R_2$ are independently H, straight chain alkyl of 1 to 6 carbon atoms, branched alkyl of 3 to 6 carbon atoms, cycloalkyl of 3 to 6 carbon atoms, alkoxycarbonyl of 1 to 6 carbon atoms, alkylcarbonyl of 1 to 6 carbon atoms, aminocarbonyl, or alkylaminocarbonyl of 1 to 4 carbon atoms;

$R_1$, $R_3$, $R_4$ and $R_5$ are independently H, straight chain alkyl of 1 to 4 carbon atoms, branched alkyl of 3 to 6 carbon atoms, cycloalkyl of 3 to 8 carbon atoms, halogen, alkoxy group of 1 to 4 carbon atoms, haloalkyl of 1 to 4 carbon atoms, hydroxy, nitro, amino, sulfonyl, cyano, carboxy, alkoxycarbonyl of 1 to 4 carbon atoms, alkylcarbonyl of 1 to 4 carbon atoms, aminocarbonyl, or alkylaminocarbonyl of 1 to 4 carbon atoms;

forms or a pharmaceutically acceptable salt thereof.

24. A compound of claim 22 wherein:

X is N—R or O;

n is an integer of 0 to 4;

R and $R_2$ are independently H, straight chain alkyl of 1 to 6 carbon atoms, branched alkyl of 3 to 6 carbon atoms, cycloalkyl of 3 to 6 carbon atoms, alkoxycarbonyl of 1 to 6 carbon atoms, alkylcarbonyl of 1 to 6 carbon atoms, aminocarbonyl, or alkylaminocarbonyl of 1 to 4 carbon atoms;

$R_1$, $R_3$, $R_4$ and $R_5$ are independently H, straight chain alkyl of 1 to 4 carbon atoms, branched alkyl of 3 to 6 carbon atoms, cycloalkyl of 3 to 8 carbon atoms, halogen, alkoxy group of 1 to 4 carbon atoms, haloalkyl of 1 to 4 carbon atoms, hydroxy, nitro, amino, sulfonyl, cyano, carboxy, alkoxycarbonyl of 1 to 4 carbon atoms, alkylcarbonyl of 1 to 4 carbon atoms, aminocarbonyl, or alkylaminocarbonyl of 1 to 4 carbon atoms;

forms or a pharmaceutically acceptable salt thereof.

25. A compound of claim 23 wherein:

X is N—R;

R is H, straight chain alkyl of 1 to 4 carbon atoms or branched alkyl of 3 to 6 carbon atoms; and $R_1$, $R_2$, $R_3$, $R_4$ and $R_5$ are as defined in claim 23; forms or a pharmaceutically acceptable salt thereof.

26. A method of treating anxiety in a mammal, the method comprising administering to a mammal in need thereof a pharmaceutically effective amount of a compound of claim 1, or a pharmaceutically acceptable salt thereof.

27. A method of treating depression in a mammal, the method comprising administering to a mammal in need thereof a pharmaceutically effective amount of a compound of claim 1, or a pharmaceutically acceptable salt thereof.

28. A pharmaceutical composition comprising a pharmaceutically effective amount of a compound of claim 1, or a pharmaceutically acceptable salt thereof, and a pharmaceutically acceptable carrier or excipient.

* * * * *